United States Patent
Shim et al.

(10) Patent No.: US 9,598,675 B2
(45) Date of Patent: Mar. 21, 2017

(54) METHOD FOR PREPARING MESENCHYMAL STEM CELL-LIKE CELLS AND CARDIOMYOCYTE-LIKE CELLS

(71) Applicant: SINGAPORE HEALTH SERVICES PTE LTD, Singapore (SG)

(72) Inventors: Winston Se Ngie Shim, Singapore (SG); Heming Wei, Singapore (SG)

(73) Assignee: SINGAPORE HEALTH SERVICES PTE LTD, Singapore (SG)

( * ) Notice: Subject to any disclaimer, the term of this patent is extended or adjusted under 35 U.S.C. 154(b) by 14 days.

(21) Appl. No.: 14/351,798

(22) PCT Filed: Oct. 12, 2012

(86) PCT No.: PCT/SG2012/000384
§ 371 (c)(1),
(2) Date: Apr. 14, 2014

(87) PCT Pub. No.: WO2013/055297
PCT Pub. Date: Apr. 18, 2013

(65) Prior Publication Data
US 2014/0314725 A1 Oct. 23, 2014

(30) Foreign Application Priority Data
Oct. 13, 2011 (SG) ................ 201107497-8

(51) Int. Cl.
| | | |
|---|---|---|
| *C12N 15/00* | (2006.01) | |
| *C12N 5/077* | (2010.01) | |
| *C12N 5/0775* | (2010.01) | |
| *A61K 35/545* | (2015.01) | |
| *A61K 35/34* | (2015.01) | |

(52) U.S. Cl.
CPC .......... *C12N 5/0657* (2013.01); *A61K 35/34* (2013.01); *A61K 35/545* (2013.01); *C12N 5/0662* (2013.01); *C12N 5/0663* (2013.01); *C12N 5/0664* (2013.01); *C12N 5/0665* (2013.01); *C12N 5/0666* (2013.01); *C12N 5/0667* (2013.01); *C12N 5/0668* (2013.01); *C12N 2500/25* (2013.01); *C12N 2500/32* (2013.01); *C12N 2500/34* (2013.01); *C12N 2500/44* (2013.01); *C12N 2500/90* (2013.01); *C12N 2501/727* (2013.01)

(58) Field of Classification Search
CPC C12N 5/0657; C12N 5/0606; C12N 2500/90; C12N 2500/25; C12N 5/0696; C12N 2500/99; C12N 2506/45; C12N 2533/52; C12N 2533/54; C12N 2501/33; C12N 2502/02; C12N 5/0603; C12N 5/0662; C12N 2502/1358; C12N 2502/1394; C12N 5/0663; C12N 2531/00; C12N 5/0075; C12N 2501/727; C12N 2533/32; C12N 2533/78; C12N 2533/80; C12N 2533/90; C12N 5/0623; C12N 5/0664; C12N 5/0665; C12N 5/0666; C12N 5/0667; C12N 5/0668; A61K 35/12; A61K 35/34; A61K 35/545

See application file for complete search history.

(56) References Cited

U.S. PATENT DOCUMENTS

| | | |
|---|---|---|
| 2004/0071665 A1 | 4/2004 | Xiao et al. |
| 2005/0112104 A1 | 5/2005 | Pittenger et al. |

FOREIGN PATENT DOCUMENTS

WO 2007075056 A1 7/2007

OTHER PUBLICATIONS

Mehta et al. Intrinsic properties and external factors determine the differentiation bias of human embryonic stem cell lines. Cell Biology International, 2010, vol. 34, pp. 1021-1031.*
Thermo Fischer Scientific, DMEM Formulation, 2015.*
Fusaki et al. Efcient induction of transgene-free human pluripotent stem cells using a vector based on Sendai virus, an RNA virus that does not integrate into the host genome . Proc. Japanese Academy, 2009, Ser. B, vol. 85, pp. 348-362.*
Van Orman et al. hESC-Derived Definitive Endoderm Induces Cardiomyogenesis in Human Embryonic Stem Cells, FASEB J, Apr. 24, 2010 (Meeting Abstract Supplement) 175.2.*
Xu et al. Characterization and Enrichment of Cardiomyocytes Derived From Human Embryonic Stem CellsCirculation Research, 2002; vol. 91, pp. 501-508.*
Caspi et al. 'Transplantation of Human Embryonic Stem Cell-Derived Cardiomyocytes Improves Myocardial Performance in Infarcted Rat Hearts'. Journal of the American College of Cardiology. 2007, vol. 50, No. 19, pp. 1884-1893.
Giuliani et al. 'Human Mesenchymal Stem Cells Derived from Induced Pluripotent Stem Cells Down-regulate NK-Cell Cytolytic Machinery'. Blood. 2011, vol. 118, pp. 3254-3262.
He et al. 'Human Embryonic Stem Cells Develop Into Multiple Types of Cardiac Myocytes: Action Potential Characterization'. Circulation Research. 2003, vol. 93, pp. 32-39.
Kim et al. 'Specific Association of Human Telomerase Activity with Immortal Cells and Cancer'. Science. 1994, vol. 266, pp. 2011-2015.
Lian et al. 'Derivation of Clinically Compliant MSCs From CD105+, CD24− Differentiated Human ESCs'. Stem Cells. 2007, vol. 25, pp. 425-436.

(Continued)

Primary Examiner — Deborah Crouch
(74) Attorney, Agent, or Firm — Brian C. Trinque; Lathrop & Gage LLP

(57) ABSTRACT

The present invention provides a method for preparing mesenchymal stem cell-like cells and cardiomyocyte-like cells from induced pluripotent stem cells. With the method, embryoid bodies are first formed from induced pluripotent stem cells in a non-adherent substrate. The embryoid bodies are then contacted with a serum-free and insulin-free medium comprising a p38-MAPK inhibitor to form aggregates of contracting embryoid bodies. The contracting embryoid body aggregate(s) are then induced to form mesenchymal stem-cell-like cells and aggregates of cardiomyocyte-like stem cells with a medium comprising ≤5% serum in a cell-culture treated substrate. The cardiomyocyte-like cells and the mesenchymal stem-cell like cells may be separated to give isolated populations of each cell type. The population of cardiomyocyte-like cells and mesenchymal stem-cell like cells and the isolated population of each cell type may be used for replacing cells. In particular, the cells may be used for replacing cells in cardiac repair and/or cardiac therapy.

15 Claims, 8 Drawing Sheets

(56) References Cited

OTHER PUBLICATIONS

Lian et al. 'Functional Mesenchymal Stem Cells Derived From Human Induced Pluripotent Stem Cells Attenuate Limb Ischemia in Mice'. Circulation. 2010, vol. 121, pp. 1113-1123.

Mehta et al. 'Pharmacological Response of Human Cardiomyocytes Derived from Virus-Free Induced Pluripotent Stem Cells'. Cardiovascular Research. 2011. vol. 91, pp. 577-586.

Takahashi et al. 'Induction of Pluripotent Stem Cells from Mouse Embryonic and Adult Fibroblast Cultures by Defined Factors'. Cell. 2006, vol. 126, pp. 663-676.

Tran et al. 'Efficient Differentiation of Human Pluripotent Stem Cells into Mesenchymal Stem Cells by Modulating Intracellular Signaling Pathways in a Feeder/Serum-free System'. Stem Cells and Development. 2012, vol. 21, No. 7, pp. 1165-1175.

Wei et al. 'One-Step Derivation of Cardiomyocytes and Mesenchymal Stem Cells from Human Pluripotent Stem Cells'. Stem Cell Research. 2012, vol. 9, No. 2, pp. 87-100.

Caja, et al "The Transforming Growth Factor-Beta (TGF-b) Mediates Acquisition of a Mesenchymal Stem Cell-Like Phenotype in Human Liver Cells" Journal of Cellular Physiology, 2010, pp. 1214-1223.

Lu, et al. "Cardiomyocyte Differentiation of Rat Bone Marrow Multipotent Progenitor Cells is Associated with Downregulation of Oct-4 Expression" Tissue Engineering: Part A, 2010, v16:10, pp. 3111-3117.

Van Ginneken and Fijnvandraat "Electrophysiological Properties of Embryonic Stem Cells During Differentiation Into Cardiomyocyte-Like Cell Types" Methods in Molecular Biology 403: Patch-Clamp Methods and Protocols, pp. 211-217.

Van Orman, et al. "Induction fo Cardiomyogenesis in Human Embryonic Stem Cells by Human Embryonic Stem Cell-Derived Definitive Endoderm" Stem Cells and Development, 2012, v21:6, pp. 987-994.

* cited by examiner

METHOD FOR PREPARING MESENCHYMAL STEM CELL-LIKE CELLS AND CARDIOMYOCYTE-LIKE CELLS

RELATED APPLICATIONS

This application is a 35 U.S.C. §371 filing of International Application No. PCT/SG2012/000384, filed Oct. 12, 2012, which claims priority to Singapore Patent Application No. 201107497-8, filed Oct. 13, 2011, each of which is incorporated herein by reference in its entirety.

FIELD OF THE INVENTION

The present invention relates to stem cell technology, for example human induced pluripotent stem cells (hiPSC) derivatives. The derivatives may be used for in vivo studies of cardiovascular disease (preclinical studies) with potential cell therapy for patients.

BACKGROUND OF THE INVENTION

Cardiomyocytes (CMs) and mesenchymal stem cells (MSCs) are two fundamental cell lineages for cardiac repair via cardiomyogenesis and angiogenesis, respectively. While functional CMs are possible to be generated from pluripotent stem cells (PSCs) including human embryonic stem cells (hESCs) and induced pluripotent stem cells (iPSCs). MSCs derived from PSCs possess much higher self-renewal potential with superior functions in vivo. CMs and MSCs derived from patient-derived human induced pluripotent stem cells (hiPSCs) are immunocompatible and thus hold, a great potential in clinical applications. At present, CMs and MSCs are separately derived from hiPSCs or hESCs and the methods require cumbersome multi-step and expensive procedures that are poorly controlled. Moreover, the quality of MSCs could be compromised if the differentiation is initiated from poor hESCs/hiPSCs with spontaneous differentiation.

To date, different approaches have been adopted in generating MSCs from hESCs. In most of the cases, hESCs cultured with feeder-free conditions were directly differentiated into MSC-like cells in medium similar to that for hESCs but with the supplementation of more bovine fibroblast growth factor (bFGF) and epithelial growth factor (EGF). Homogeneous MSCs were obtained after several passaging and FACS-based cell sorting, a process that could take a few weeks.

Alternatively, hESC-MSCs were derived from Day 4 and 10 embryoid bodies (EBs) that were plated onto gelatin-coated tissue culture plates and the MSC-like cells migrated from EBs and were subcultured.

The homogeneity of hESC/hiPSC-derived MSCs is a key issue for the clinical application of hiPSC-MSCs as they are derived from highly pluripotent stem cells which are capable of teratoma formation in vivo. To address such concern, a more defined method for the generating of potentially clinical applicable MSCs was developed. In brief, hESCs and hiPSCs were directly differentiated in a defined medium containing growth factors, fibroblast growth factor (FGF) and platelet derived growth factor (PDGF) or epidermal growth factor (EGF). Next, homogeneous MSCs were obtained either by FACS-based cell sorting for CD24−/CD105+ or by limited dilution to generate single-cell derived colonies. After all, all of the above methods were developed from established hESC lines and little details were given on the differentiation efficiency. In addition, these methods require expensive consumables (growth factors and antibodies) and high-end equipment (FACS sorter).

Since hiPSC colonies are generally considered as less stable than that of hESCs and are more prone to spontaneous differentiation, the generation of high quality hiPSC-MSCs could be more challenging. To date, only the method of Lian et al., 2007 (direct differentiation plus CD24−/CD105+ sorting) has been used to differentiate hiPSCs into MSCs.

Cardiac cell therapy requires not only functional cardiomyocytes (CMs), but also pro-angiogenic cell lineages such as mesenchymal stem/stromal cells (MSCs) for effective cardiac repair. However, clinical application of CMs has been hampered by the lack of autologous functional human CMs where cardiac biopsy failed to yield CMs that can be expanded in culture. On the other hand, MSCs derived from adult tissues (bone marrow and adipose tissue) have shown therapeutic potential. Currently, hiPSC-CM and hiPSC-MSCs are separately derived from disparate mesodermal differentiation protocols which are tedious and time-consuming. However, adult tissue-derived MSCs are limited in their clinical application due to their poor self-renewal potential and functional competency in the elderly individuals and in patients with chronic diseases. Although human embryonic stem cells (hESCs) are capable of generating functional CMs and MSCs, their clinical applications have been hampered by immunoreactivity and ethical issues.

An alternative means of deriving MSCs is desirable for successful therapeutic applications together with CMs, for example in autologous cardiac cell therapy.

SUMMARY OF THE INVENTION

The invention relates to cell culture and uses thereof. Accordingly, the present invention provides a method for preparing mesenchymal stem cell-like cells and cardiomyocyte-like cells comprising the steps of:
(i) providing one or more induced pluripotent stem cells;
(ii) forming one or more embryoid bodies from the induced pluripotent stem cells using a non-adherent substrate;
(iii) contacting the embryoid bodies with serum-free and insulin-free medium comprising a p38-MAPK inhibitor to form aggregates of contracting embryoid body cells;
(iv) transferring at least one contracting embryoid body aggregrate to a cell-culture treated substrate and contacting the contracting embryoid body aggregates with a medium comprising ≤5% serum to form a population of cells comprising mesenchymal stem cell-like cells and aggregates of cardiomyocyte-like cells, wherein the population of cells is substantially adhered to the substrate.

The present invention also relates to a population of cells comprising mesenchymal stem cell-like cells and cardiomyocyte-like cells obtained by the method as described herein.

The method further comprises detaching the adhered cells from the substrate and collecting the detached cells as a population of mesenchymal stem cell-like cells and cardiomyocyte-like cells.

Alternatively, the aggregates of cardiomyocyte-like cells and the mesenchymal stem cell-like cells may be separated to give a first isolated population of cardiomyocyte-like cells and a second isolated population of mesenchymal stem cell-like cells.

Accordingly, the invention also includes an isolated population of cells comprising cardiomyocyte-like cells obtained by the method as described herein.

The invention further includes an isolated population of cells comprising mesenchymal stem cell-like cells obtained by the method as described herein.

A: Immunofluorescent staining of iPSC (1) with antibodies against Oct-4, SSEA-4, TRA-1-81, and TRA-1-60. B: RT-PCR of the expression of endogenous genes Oct-4, Sox-2, c-Myc and Klf-4 in iPSC (1) and (2) while H9 hESCs and dermal FBs served as control. C: Hematoxylin and eosin staining of teratoma derived from iPSC (1) in NOD-SCID mice after 12 weeks. Characteristic tissue structures representing 3-primitary germ layers are: glandular structure for endoderm (C1), Smooth muscle tissue for mesoderm (C2) and Neural epithelia for ectoderm (C3). D: Karyotypes of iPSC (1), (2) and H9 hESCs.

Figure 2:
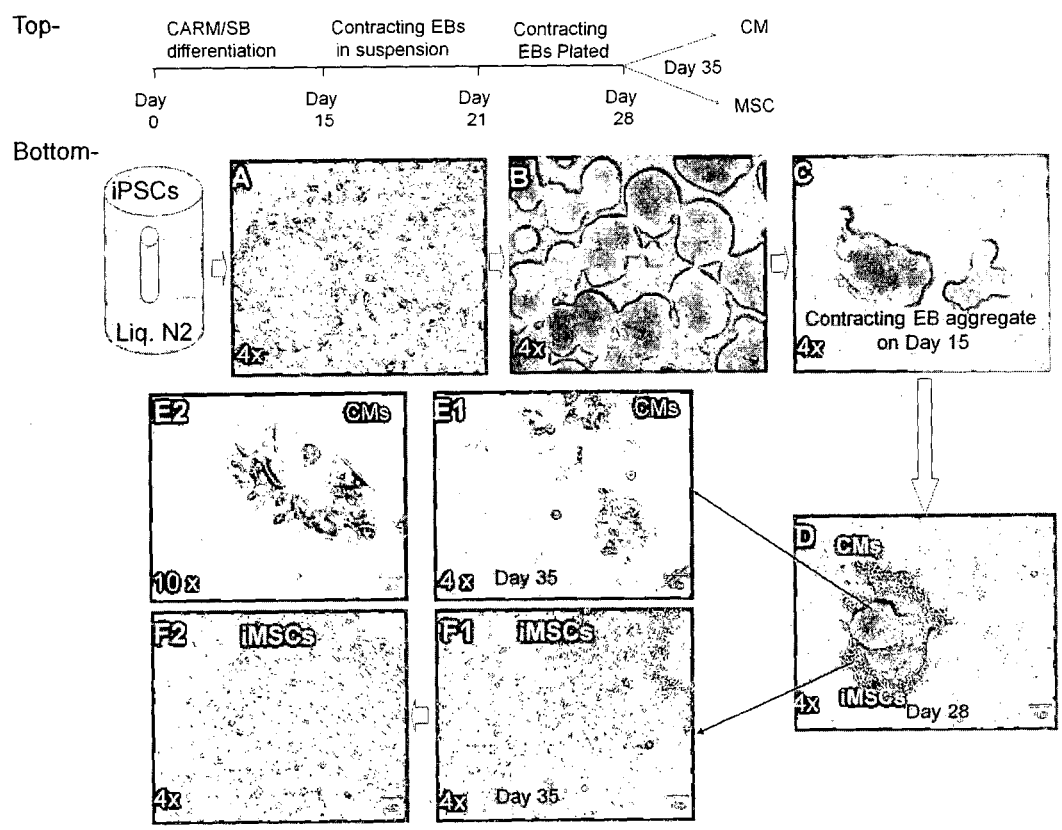

FIG. 2 The process of co-generation of hiPSC-CMs and hiPSC-MSCs by the present CARM/SB method Top—Flow chart of the process of co-generation of hiPSC-CMs and hiPSC-MSCs. B: Graphic demonstration of the process of co-generation of hiPSC-CMs and hiPSC-MSCs by the present CARM/SB method.

Bottom—A: undifferentiated colonies of hiPSCs on MEF. B: EBs formed in suspension culture. Day 2 after differentiation. C: EB-aggregates (contracting) in suspension culture. Day 12 after differentiation. D: EB-aggregates (contracting) plated. Outgrowth of CMs and MSCs were indicated. E: CMs derived from the contracting Outgrowth of plated EB-aggregates. F: MSCs derived from the contracting Outgrowth of plated EB-aggregates.

Figure 3:
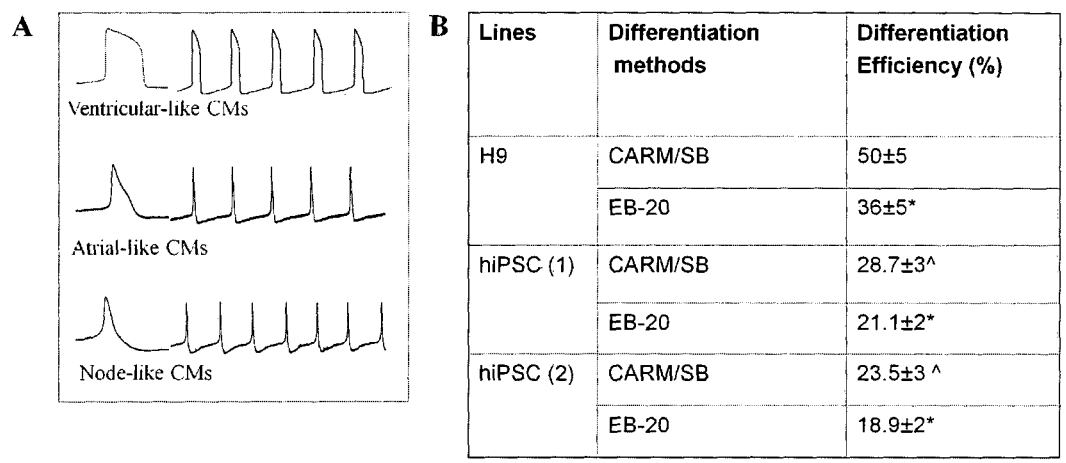

FIG. 3 Characterization of hiPSC-CMs

A: Cardiac action potential (AP) recorded on single hiPSC-CM by whole cell Patch-Clamp assay. All three subtypes of cardiomyocytes were identified by unique AP patterns. B: Comparison of cardiac differentiation efficiency (contracting EB aggregates/total EB aggregates) % between the CARM/SB and EB-20 methods. * $p<0.05$ (EB-20 vs. CARM/SB protocol) and ˆ $p<0.05$ (hiPSCs vs. H9 hESCs).

Figure 4:
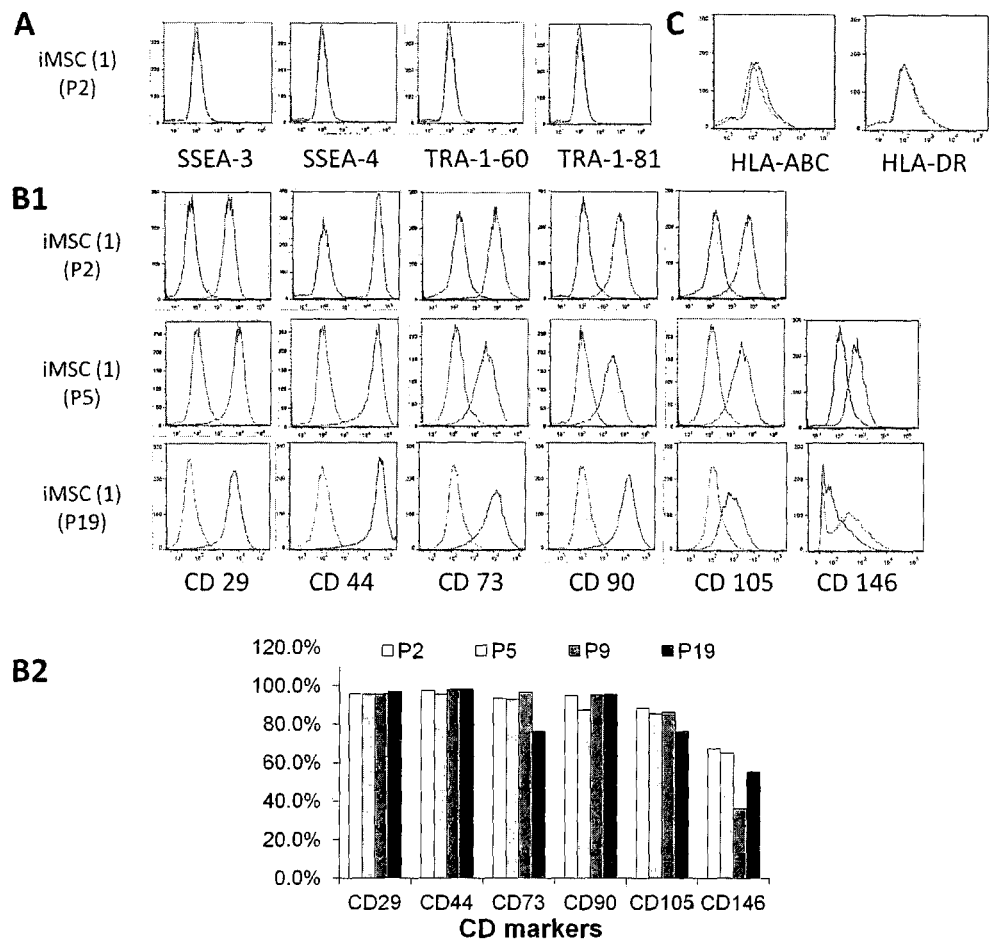

FIG. 4 Characterization of iPSC-MSCs by Flow Cytometry assay and karyotyping iMSC (1) at passage 2, 5, and 9 and 19 were characterized by flow cytometry assay. A: Expression of pluripotent markers detected with passage 2 iMSC (1). B: typical MSC markers determined with iMSC (1) at passage 2, 5, and 19. B1: typical overlay flow images. B2: comparison of the passage-impact on the expression of common MSC-markers. C: HLA-ABC and HLA-DL markers detected with passage 2 iMSC (1).

Figure 5:
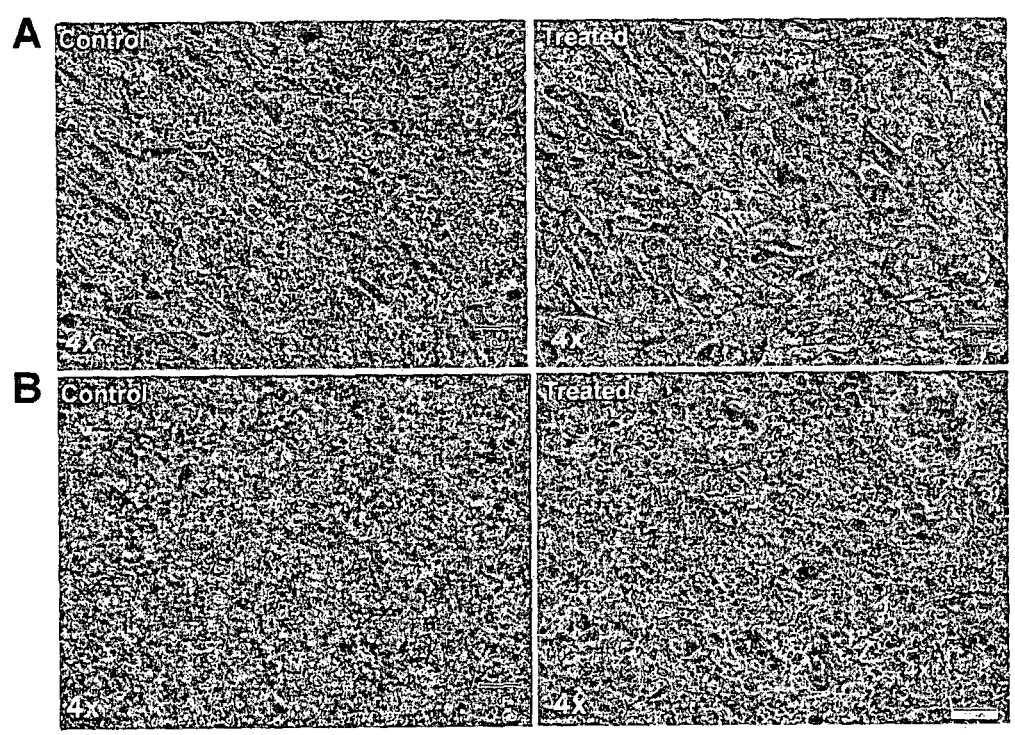

FIG. 5 Adipogenic and osteogenic differentiation of hiPSC-MSCs

A: hiPSC-MSC (1) at passage 7 differentiated into adipocyte-like cells verified by Oil-Red-O Staining. B: hiPSC-MSC (1) at passage 7 differentiated into osteocyte-like cells verified by Alizarin Red S Staining.

Figure 6:
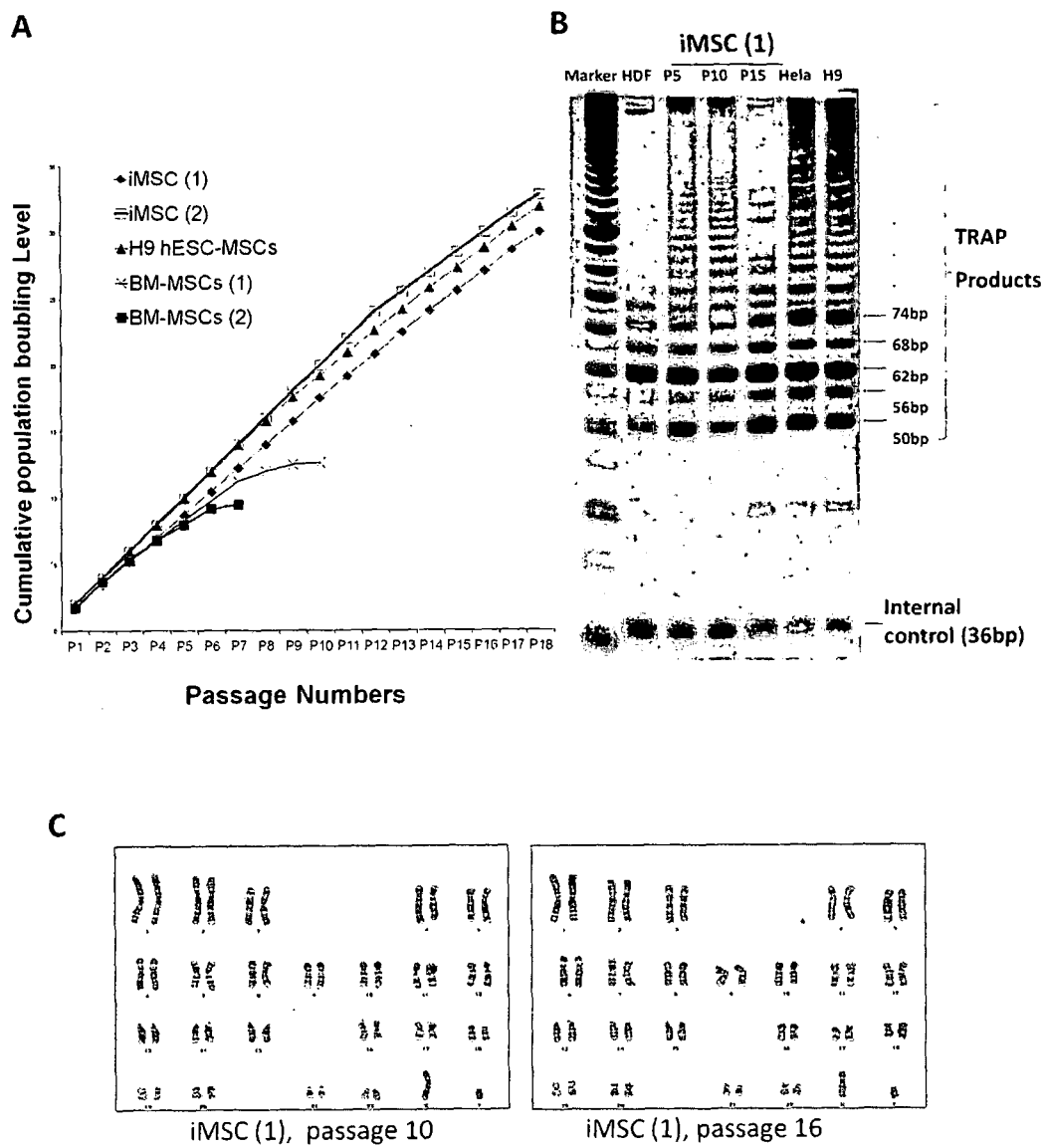

FIG. 6 Growth kinetics and telomerase activity of hiPSC-MSCs

A: Cumulative population doubling levels from iMSC (1) and hESC-MSCs, BM-MSCs from healthy (BM-MSC (1)) and myocardial infarction patient (BM-MSC (2)) were recorded and compared. B: Telomerase activity in iMSC (1) of different passages was detected. Human dermal fibroblast (HDF) at passage 2 was used as negative control while— HeLa cell and H9 ES cell were used as positive controls. The right arrows indicate the bands of TRAP products and internal control. C: Normal karyotype observed with iMSC (1) at passage 10 and 16.

Figure 7:
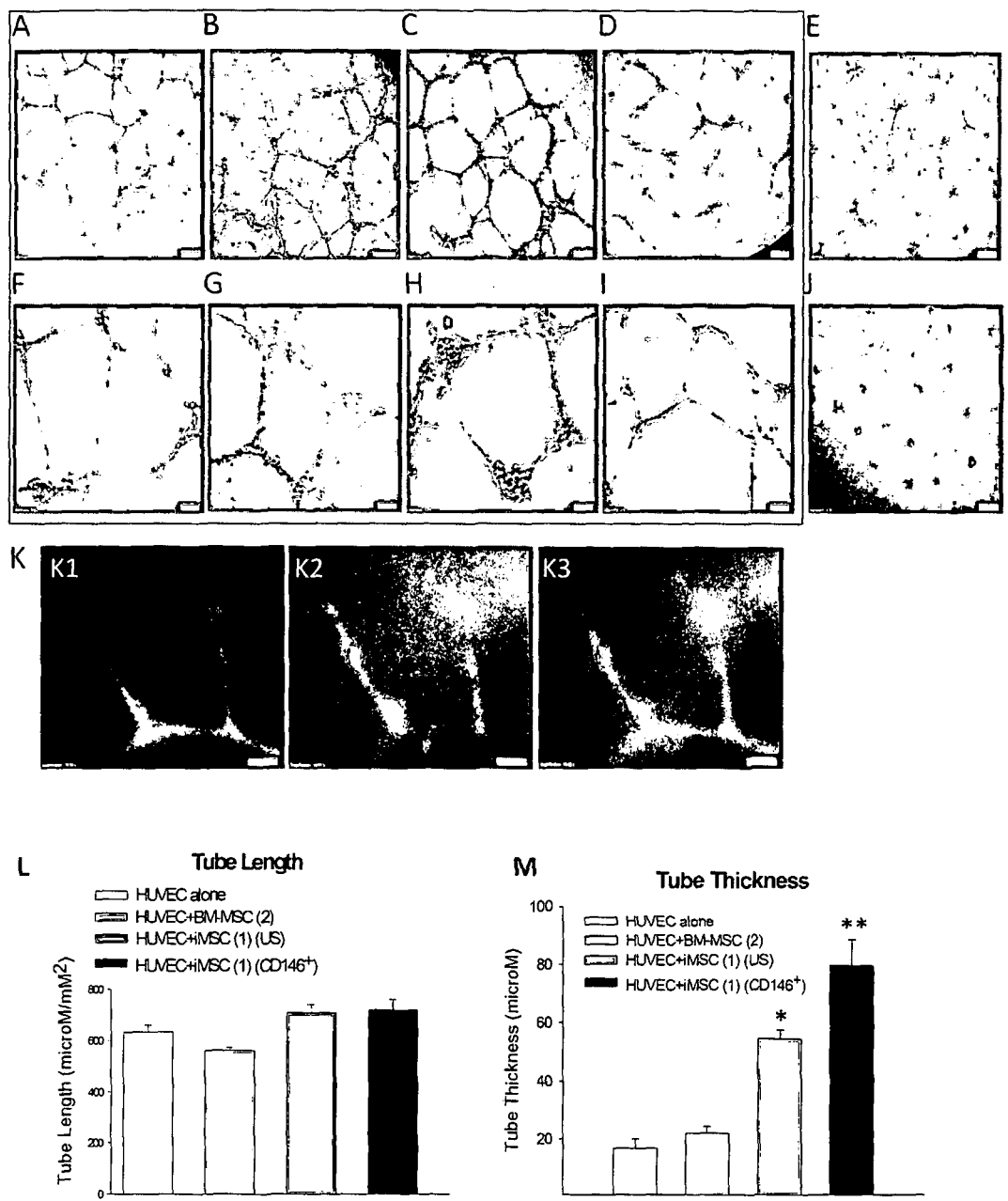

FIG. 7 Endothelial tube formation assay

A, F: HUVECs (Passage 3) only (4× and 10×). B,G: HUVECs (Passage 3)+hiPSC-MSCs (Passage 11) (4× and 10×). C,H: HUVECs (Passage 3)+hiPSC-MSCs (Sorted, CD44+/CD146+) (4× and 10×). D,I: HUVECs (Passage 3)+BM-MSC (Passage 3) (4× and 10×). E: hiPSC-MSCs (Passage 11) only. J: BM-MSCs (2) (Passage) only. K: Fluorescent imaging of the tube structure. K1-HUVECs (Green). K2-MSCs (red) and K3-overlay. L: Quantification of tube length by Image J. * $p<0.05$. ** $p<0.01$. M: Quantification of tube thickness by Image J. * $p<0.05$. ** $p<0.01$.

Figure 8:
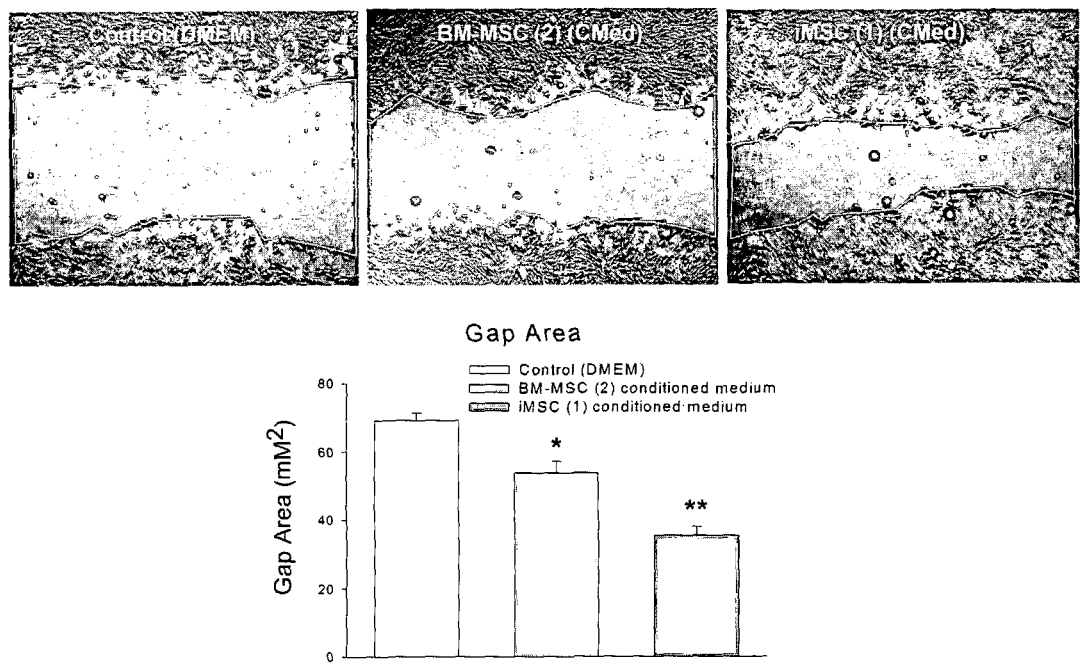

FIG. 8 Wound-healing assay

Upper panel: Left—Human neonatal dermal fibroblasts (Passage 8)+DMEM;

Middle—Human neonatal dermal fibroblasts (Passage 8)+hiPSC (1)-MSC(P8) conditioned medium (CMed). Right-Human neonatal dermal fibroblasts (Passage 8)+BM-MSC(2) (P4) conditioned medium (CMed). Bottom: Quantification of the gap area. * $p<0.05$. ** $p<0.01$. Images were taken by a Leica Stereomicroscope, 3.6×.

DEFINITIONS

The term "cardiomyocyte-like cells" is intended to mean cells sharing features with cardiomyocytes. Cardiomyocyte-like cells are further defined by morphological characteristics as well as by specific marker characteristics.

As used herein the term "atrial-like cardiomyocytes" is intended to mean cells with the following action potential characteristics: membrane resting potential (MRP): −50 to −80 mV, and duration: <150 ms.

As used herein the term "nodal-like cardiomyocytes" is intended to mean cells with the following action potential characteristics: membrane resting potential (MRP): −40 to −60 mV; duration: 80-130 ms, and a pronounced phase 4 depolarization.

As used herein the term "ventricular-like cardiomyocytes" is intended to mean cells with the following action potential characteristics: membrane resting potential (MRP): −50 to −80 mV, duration: >150 ms, and a pronounced plateau phase.

An "embryoid body" refers to an aggregate of cells derived from pluripotent cells, where cell aggregation can be initiated by any method that prevents the cells from adhering to a surface to form typical colony growth.

As used herein, the term "homogeneous" is used to describe cell populations which are substantially of the same developmental stage and exhibit substantially the same phenotype. Such a homogeneous population may comprise greater than about 90% of substantially the same cells, or at least about 92%, 94%, 96%, 98%, 99%, 99.9% or 100% of substantially the same cells.

The term "induced pluripotent stem cells" refers to a pluripotent stem cell derived from a non-pluripotent cell (e.g. an adult somatic cell). Induced pluripotent stem cells are identical to embryonic stem cells in the ability to form any adult cell, but are not derived from an embryo.

As used herein, the term "insulin-free" is used to describe a culture and/or a culture medium substantially without any insulin.

"Mesenchymal stem cells" refer to multipotent stem cells that can differentiate into a variety of cell types including: osteoblasts (bone cells), chondrocytes (cartilage cells) and adipocytes (fat cells).

The term "mesenchymal stem cell-like cells" is intended to mean cells sharing features with mesenchymal stem cells. For example, mesenchymal stem cell-like cells share growth characteristics, biochemical activity and markers resembling that of mesenchymal stem cells.

A "cell-culture treated substrate" refers to a substrate that has been physically or chemically treated or conditioned to promote or facilitate cell adhesion to the substrate, or to otherwise include a cell attachment factor.

A "non-adherent substrate" refers to a substrate that has not been treated to promote cell attachment and lacks any cell attachment factors on its surface that promote adhesion of the cells thereto. The substrate may be in the form of a culture vessel, for example a petri dish, flask, bottle, plate, tube, vial, etc, which can be welled or unwelled. Other substrates, such as two-dimensional or three-dimensional scaffolds, implants, microcarriers (e.g., beads composed of glass, plastic, or other materials), fiber beds, hollow fibers, stacked plate modules, or cell factories can also be utilized. Typically, the substrate has a surface topography that is sufficiently smooth (lacking roughness) so as to prevent cell attachment. Therefore, random roughness, grooves, and pillars/spikes are not present or their presence is minimized.

As used herein, the term "pluripotent" refers to the potential of a stem cell to make any differentiated cell of an organism. Pluripotent stem cells can give rise to any fetal or adult cell type. However, alone they cannot develop into a fetal or adult organism because they lack the potential to contribute to extraembryonic tissue, such as the placenta.

As used herein, the term "serum-free" is used to describe a culture and/or a culture medium substantially without any serum or plasma.

As used herein, "substantially without" means present in a concentration that is less than about 1%, preferably less than about 0.5%, more preferably less than about 0.1%, most preferably completely absent.

DETAILED DESCRIPTION OF THE INVENTION

In the present invention, induced human pluripotent stem cells are differentiated to form a population of mesenchymal stem cell-like cells and cardiomyocyte-like cells. Accordingly, the invention provides a method for preparing mesenchymal stem cell-like cells and cardiomyocyte-like cells comprising the steps of:
(i) providing one or more induced pluripotent stem cells;
(ii) forming one or more embryoid bodies from the induced pluripotent stem cells using a non-adherent substrate;
(iii) contacting the embryoid bodies with serum-free and insulin-free medium comprising a p38-MAPK inhibitor to form aggregates of contracting embryoid body cells;
(iv) transferring at least one contracting embryoid body aggregrate to a cell-culture treated substrate and contacting the contracting embryoid body aggregates with a medium comprising ≤5% serum to form a population of cells comprising mesenchymal stem cell-like cells and aggregates of cardiomyocyte-like cells, wherein the population of cells is substantially adhered to the substrate.

The induced pluripotent stem cell(s) may be from any animal. For example, the induced pluripotent stem cells may be human. Any method of preparing induced pluripotent stem cells is applicable for the invention.

For step (ii), any suitable method may be used to form the embryoid bodies from the induced pluripotent stem cells. For example, the induced pluripotent stem cells may be contacted with a suitable culture medium to form one or more embryoid bodies. For example, the culture medium comprises Dulbecco's Modified Eagle Medium (DMEM) High Glucose, L-Glutamine, non-essential amino acids (NEAA), Selenium Transferrin and 2-mercaptoethanol. The final culture medium may comprise a suitable concentration of each component suitable for inducing embryoid body formation.

With step (iii), in order to form contracting embryoid bodies, the embryoid bodies are contacted with a serum-free and insulin-free medium comprising a p38-MAPK inhibitor. For example, the serum-free and insulin-free medium is the same as the culture medium for forming embryoid bodies described above with the addition of any suitable amount of a p38-MAPK inhibitor. The embryoid bodies may be contacted with the serum-free and insulin-free medium comprising a p38-MAPK inhibitor for a time sufficient to form contracting embryoid bodies. For example, the period of time may be at least 8 days. The period of time may also be 10 days or 11 days. The serum-free and insulin-free medium comprising the p38-MAPK inhibitor may be replaced or changed if necessary.

Any suitable p38-MAPK inhibitor may be used. For example, the p38-MAPK inhibitor includes but is not limited to SB203580 (4-[4-(4-fluorophenyl)-2-(4-methylsulfinylphenyl)-1H-imidazol-5-yl]pyridine), BIRB 796 1-[5-tert-butyl-2-(4-methylphenyl)pyrazol-3-yl]-3-[4-(2-morpholin-4-ylethoxy)naphthalen-1-yl]urea), SB202190 (4-[4-(4-fluorophenyl)-5-pyridin-4-yl-1,3-dihydroimidazol-2-ylidene]cyclohexa-2,5-dien-1-one, VX-702 6-(N-carbamoyl-2,6-difluoroanilino)-2-(2,4-difluorophenyl) pyridine-3-carboxamide), LY2228820 (5-[2-tert-butyl-4-(4-fluorophenyl)-1H-imidazol-5-yl]-3-(2,2-dimethylpropyl) imidazo[4,5-b]pyridin-2-amine; methanesulfonic acid), VX-745 (5-(2,6-dichlorophenyl)-2-(2,4-difluorophenylthio)-6H-pyrimido[1,6-b]pyridazin-6-one) or PH-797804 (3-[3-bromo-4-[(2,4-difluorophenyl)methoxy]-6-methyl-2-oxopyridin-1-yl]-N,4-dimethylbenzamide). In particular, the p38-MAPK inhibitor comprises SB203580.

For step (iv), any suitable amount of any suitable serum may be used in the medium. For example, the medium may comprise 0.5 to 5% serum. Accordingly, the medium may comprise 0.5%, 1%, 2%, 2.5%, 3%, 3.5%, 4%, 4.5% or 5% serum. In particular, the medium comprises 2% serum. The serum may comprise fetal bovine serum (FBS).

The method according to any aspect of the invention is typically performed in vitro.

The present invention also relates to a population of cells comprising mesenchymal stem cell-like cells and cardiomyocyte-like cells obtained by the method as described herein.

The method further comprises detaching the adhered cells from the substrate and collecting the detached cells as a population of mesenchymal stem cell-like cells and cardiomyocyte-like cells.

Alternatively, the aggregates of cardiomyocyte-like cells and the mesenchymal stem cell-like cells may be separated to give a first isolated population of cardiomyocyte-like cells and a second isolated population of mesenchymal stem cell-like cells. The two populations of cells may be separated by any method. For example, the two populations of cells may be physically separated. In particular, the cardiomyocyte-like cells may be physically and/or mechanically removed from the population comprising the two cell types.

Accordingly, the invention also includes an isolated population of cells comprising cardiomyocyte-like cells obtained by the method as described herein. The isolated population of cardiomyocyte-like cells comprises ventricular-like, atrial-like and nodal-like cardiomyocytes.

The isolated population of cardiomyocyte-like cells may be further cultured and/or maintained in culture.

The invention further includes an isolated population of cells comprising mesenchymal stem cell-like cells obtained by the method as described herein. The isolated population of mesenchymal stem cell-like cells is substantially homogeneous.

The isolated population of mesenchymal stem cell-like cells may also be further cultured and/or maintained in culture.

The two isolated populations may be combined again to form a composition comprising mesenchymal stem cell-like cells and cardiomyocyte-like cells. The combination step may be performed before or after further culturing of each population of cells.

Accordingly, the invention also includes a composition comprising at least one isolated population of mesenchymal stem-cell-like cells according to any aspect of the invention and at least one isolated population of cardiomyocyte-like cells obtained according to any aspect of the invention.

The invention also includes a kit comprising at least one population of cells according to any aspect of the invention or the composition according to any aspect of the invention.

The population of cells, isolated population of cardiomyocyte-like cells, isolated population of mesenchymal stem cell-like cells and/or composition according to any aspect of the invention may be for use in cell replacement.

The invention also includes the use of at least one population of mesenchymal stem cell-like cells and cardiomyocyte-like cells, at least one isolated population of cardiomyocyte-like cells and/or at least one isolated population of mesenchymal stem cell-like cells according to any aspect of the invention for the preparation of a composition for cell replacement.

Also provided is a method comprising using at least one population of mesenchymal stem cell-like cells and cardiomyocyte-like cells, at least one isolated population of cardiomyocyte-like cells, at least one isolated population of mesenchymal stem cell-like cells obtained by a method according to any aspect of the invention to replace cells.

Further provided is a method comprising using at least one isolated population of mesenchymal stem cell-like cells obtained by a method according to any aspect of the invention and at least one isolated population of cardiomyocyte-like cells obtained by a method according to any aspect of the invention to replace cells.

In particular, the cell replacement for any aspect of the invention described herein is for cardiac repair and/or cardiac therapy.

EXAMPLES

The following examples are provided as illustrations and are not intended to be limiting of the present invention.

Example 1

We have developed an efficient methodology for the co-generation of high quality mesenchymal stem cells and cardiomyocytes from human induced pluripotent stem cells. We derived both CMs and MSCs which are of mesoderm origin and co-generated from human induced pluripotent stem cells (hiPSCs) via a pro-mesoderm differentiation strategy to yield regenerative cell types for autologous use.

Accordingly, we have successfully co-generated cardiomyocytes and high quality of MSCs in a low-cost and effective manner.

Our present serum-free and insulin-free cardiac differentiation (CARM/SB) method could be particularly useful in differentiating hiPSCs into high quality MSCs in a low-cost and effective manner.

Our present CARM/SB method does not compromise the quality of cardiomyocytes derived from hiPSCs.

Moreover, we have systematically characterized the cardiomyocytes that were co-generated with our methodology with those generated with the original method. No differences were found. All together, our protocol enables derivation of totally autologous composite tissues of cardiomyocytes and mesenchymal stem cells for cardiovascular applications Generation and Characterization of iPSC-CMs Differentiation of iPSCs into Cardiomyocytes Guided cardiac differentiation of hiPSCs was carried out via embryoid body formation in a serum-free and insulin-free cardiomyogenic medium (CARM) plus a p38-MAPK inhibitor (for example SB203580). Other p38-MAPK inhibitors may also be used.

CARM (Cardiomyogenic Medium):

DMEM High Glucose 485 ml (Gibco; Life Technologies), Penicillin-steptomycin-L-GLutamine 5 ml (final concentration 0.2 mM; Gibco; Life Technologies), NEAA 5 ml (final concentration 0.1 mM; Gibco; Life Technologies), Selenium Transferrin (100×) 5 ml (final 1%, v/v; final concentration 5.5 ug/ml transferrin/6.7 ng/ml sodium selenite; Sigma-Aldrich), 2-mercaptoethanol 3.5 ul (final concentration 0.1 mM; Gibco; Life Technologies), SB203580 (Sigma S8307-1 mg) (Add 265 µl DMSO to 1 mg generate a stock of 10 mM)

On Day 1, EBs were formed from hiPSCs as above mentioned. On Day 2, the cardiac differentiation were initiated with a serum-free and insulin-free medium named cardiomyogenic medium or CARM (containing DMEM High Glucose 485 ml, L-GLutamine 5 ml, NEAA 5 ml, Selenium Transferrin 5 ml (Sigma) and 2-mercaptoethanol 3.5 ul). SB 203580 (5 uM), a specific p38-MAPK inhibitor (Sigma) was added in CARM and kept for 4 days till Day 6. Next, the differentiation medium was changed and maintained till Day 14. Contracting EB aggregates emerged from Day 12. On Day 15, the contracting EB aggregates were picked up and plated on 0.1% gelatin-coated wells of 6-well plate or 3.5-cm Petri dishes in DMEM medium containing 2% FBS and keep for 1 weeks until the contracting CM clumps firmly attached and CM outgrowth enlarged and could be dissected out.

Characterization of iPSC-CMs

—Dissociation and characterization of CMS from EB aggregates—
—The expressions of cardiac marker of hiPSC-CMs by Immunocytochemistry assay—
—Electrophysiological characterization by action potential (APs)—
—Confocal calcium imaging for $Ca^{2+}$ transient—

Generation of hiPSC-MSCs

Establishment of iPSC-MSC Lines by which Enables the Co-Generation of CMs and MSCs hiPSC-MSCs were generated in this study by the CARM/SB method which facilitated the generation of iPSC-CMs as well. It was noted that MSC-like cells rapidly outgrew from the attached EB aggregates after Day 15 cardiac differentiation. These cells appeared to be homogeneous and they rapidly reached occupied >80% of a well of a s-well plate in ~two weeks time. After mechanical removing of the CM clumps and the non-MSC-like cells, the remaining MSC-like cells were cultured in MSC medium (DMED supplemented with 10% serum) to full confluency. Next, these cells were dissociated with Trypsin and transferred in a T25 flask (Passage 1). MSCs were further expanded in MSC medium with a 1:4 split ratio. MSCs were continually expanded to passage 20.

Characterization of iPSC-MSCs

Two lines of human bone marrow-derived MSCs were used in this study as control. BM-MSC (1) was derived from marrow mononuclear cells (DV Biologics, Costa Mesa, Calif.) while BM-MSC (2) was derived from a myocardial infarction patient recruited at National Heart Centre Singapore with a protocol approved by the Institutional Review Board of Singapore Health Science Authority.

Surface Markers Measurement and Cell Sorting—

The Flow cytometry and Fluorescent-Activated Cell Sorting (FACS) were performed with a FACS Aria™. PE, APC and FITC congregated mAbs were used to determine CD29, CD44, CD73, CD90, CD105, and CD146 expression with Passage 2, 5, 7, 9 and 19 hiPSC-MSCs. In addition, pluripotent stem cell markers SSEA-3, SSEA-4, TRA-1-60, TRA-1-81 and hematopoietic marker CD34 were measured with passage 2 hiPSC-MSCs. CD44+/CD146+ hiPSC-MSCs (Passage 6~11) were sorted out for the angiogenesis assay.

Lineage-Specific Differentiations—
Adipogenic Differentiations of hiPSC-MSCs—

Passage 7 hiPSC-MSCs were differentiated into adipocytes by MesenCult® Adipogenic Stimulatory Supplements (Human) from Stemcell Technologies®. After 21 days, differentiated cells were subjected to Oil-Red-0 staining. Control hiPSC-MSCs were cultured under the same condition without Adipogenic Stimulatory Supplements.

Osteogenic Differentiations of hiPSC-MSCs—

Passage 7 hiPSC-MSCs were differentiated into adipocytes with MesenCult® Osteogenic Stimulatory Kit (Human). After 21-28 days, differentiated cells were confirmed by Alizarin Red S Staining for Calcium. Control hiPSC-MSCs were cultured under the same condition without Osteogenic Stimulatory Supplements.

the Growth Kinetics of MSCs—

MSC were continually cultured from Passage 2 to 20. Cells were maintained in a liner growth range. After Passage 3, hiPSC-MSCs were expanded with a starting density of $1\times10^6$ cells per T75 flasks in MSC medium. Cells were split when they reached 90% confluence. Next, $1\times10^6$ viable cells were re-seeded again in a T75 culture flask and continually passaged. The cumulated population doublings level (CPDL) was calculated and plotted. The CPDL was recorded every passage and plotted over passage numbers. The formula for calculating PDL is: PDL=3.32(log(total viable cells at harvest/total viable cells at seed). In the mean time, the growth kinetics of BM-MSCs derived from two bone marrow samples was also determined.

Telomerase Activity Assay—

The telomerase activity of cultured cells was explored using TRAPEZE® telomerase detection kit (Millipore). The procedures in the manual were strictly followed In brief, the cell extracts (from a total of $5\times10^6$) were prepared from cultured iPSC-MSC cells using 3-[(3-cholamidopropyl)-dimethylammonio]-1-propanesulfonate (CHAPS) lysis buffer, and human dermal fibroblasts, HeLa cell and H9 ES cell extracts were prepared as well. Protein concentration was determined by the Bradford assay with bovine serum albumin as a standard. Detection of telomerase in cells employed the PCR-based telomeric-repeat amplification protocol (TRAP) described by Kim et al (1994), using the oligonucleotides TS and CX as forward and reverse primers respectively. PCR was performed for 27 cycles with a 30-second denaturation step at 94 degree, 30-second annealing step at 50 degree, and a 1-minute extension step at 72 degree. PCR products were resolved by electrophoresis in nondenaturing 15% polyacrylamide gels in 45 mM Tris base/45 mM boric acid/1 mM EDTA for 1800 V·hr. Gels were stained with 1% SYBR gold for 20 minutes and exposed to UV illumination for documentation.

Teratoma Formation Assay—

As above-mentioned, $2\times10^6$ of passage 4 hiPSC-MSCs were injected into the hind limb muscle (im) and kidney capsule of NOD-SCID mice and allowed 12-16 weeks to form teratoma.

Functional Evaluations of hiPSC-MSCs
Angiogenesis (In Vitro) by Endothelial-Tube Formation Assay—

Endothelial-tube formation assay was conducted following previous reports with some modifications. In brief, Matrigel (BD) of 75 μL was added in each wells of a 96-well plate. A total number of $0.6\times10^4$ of unsorted and CD44+/CD146+ iPSC-MSCs (P6-P11) and unsorted BM-MSCs (P3) were seeded on Matrigel together with $1.25\times10^4$ human umbilical vein endothelial cells or HUVECs at P3. After 24 hours, vessel-like network structures were examined under light microscopy and images were taken. Next, cells were fixed and the vasculature was stained by mouse anti-human-CD31 monoclonal antibody for HUVECs and anti-human alpha-Smooth Muscle Actin (α-SMA) for MSCs and images were taken with a fluorescent microscope. Vasculature density was calculated as the lengths and thickness of vessels/mm$^2$ using the Image J software.

Wound-Healing Assay—

Human neonatal dermal fibroblasts (P8) were cultured to 90% confluence and a 2-mm wide gap was created by scratching. Next, the conditioned-medium of hiPSC-MSCs (P6) and BM-MSC(P4) were collected after 24 hours culturing in serum-free DMEM and added to the fibroblasts culture and incubated for 24 hours. Light microscopy images were taken and the remaining gap area was measured and quantified by Image J software.

Preparation of conditioned-medium of hiPSC-MSCs and BM-MSCs: Cells were cultured to 80% confluency. Then the cultural media were removed and cells washed with DPBS (Ca2+ and Mg2+-free). Next, serum-free DMEM were added to the cells and incubated over night. Next, the medium was collected.

Functional Benefits Evaluations of iPSC-Derived MSCs and Cardiomyocytes-Like Cells In Vivo—

Myocardial infarction model was generated in severe combined immunodeficiency (SCID) mice by ligation of the left anterior descending artery or LAD. Next, a total of $2\times10^5$ iPSC-derived MSCs, or $2\times10^5$ iPSC-derived cardiomyocytes-like cells, or $1\times10^5$ iPS-derived MSCs in combination of $1\times10^5$ iPSC-derived cardiomyocytes-like cells were injected into the peri-infarct site. iPSC-derived MSCs were labeled with green fluorescent protein (GFP) so they could be better tracked in the post-infarct heart. Cardiac hemodynamic were performed at 8 weeks post transplantation by echocardiography.

Our methodology possesses several important advantages over existing methodologies by which cardiomyocytes and MSCs were generated separately. It enables effective generation of a large number and yet homogeneous MSCs from single EB aggregates.

Firstly, the Quality of Our MSCs is Guaranteed as they are Generated Exclusively from Good Quality Undifferentiated hESCs/hiPSCs.

Four and eight days EBs are not fully differentiated and not ready to give rise to contracting cardiomyocytes. In contrast, all contracting cardiomyocytes will emerge with 15-21 days EBs. On the other hand, direct differentiation of hESCs or hiPSCs is achieved without EB formation process. Poorly maintained hiPSCs and hESCs will undergo spontaneous differentiation before EB formation. Thus, EB formation and cardiac differentiation could serve as index of good quality of hiPSCs and hESCs.

Comparing to the existing methodologies in generating MSCs from hESCs and hiPSCs via direct differentiation or from 4-8 days EBs, our MSCs are generated from day 15-21 contracting EBs which clearly indicates that our MSCs are derived from good quality hiPSCs or hESCs. The co-generation of cardiomyocytes will serve as a quality control step proving that our MSCs are generated from good quality hiPSCs or hESCs. This advantage is particularly important to hiPSCs as they are more prone to spontaneous differentiation than hESCs. Moreover, unlike the established hESC lines (H1, H3, H7 and H9) which are capable of cardiac differentiation, cardiogenic ability of most hiPSC lines generated from a human patient is yet to be defined.

Secondly, Our MSCs are Homogeneous and May Ready for Use without Sorting.

Our MSCs become homogeneous at very early stage (Passage 2, as proven by flow cytometry assay).

Thus our MSCs that are generated from good quality undifferentiated hESCs/hiPSCs are ready to use without further FACS-based cell sorting.

Thirdly, a Large Number of MSCs can be Generated from Single EBs

Around ⅓ of contracting EB aggregates could give raise to a large number of homogeneous MSCs (Up to $10^9$ at Passage 6) within 4 weeks. Thus sufficient MSCs (for one time delivery) could be generated from a few contracting EBs. Moreover, with pre-transplantation testing, different lines of MSCs derived from different EBs could allow the selection for the best lines, which is impossible with other methodologies outlined previously.

Lastly, Low-Cost

While it may take similar time to generate MSCs with our methodology, the cost for generating MSCs with our approach is substantially lower than the existing methodologies.

With our efficient methodology, we are able to co-generate a large number of biocompatible and high quality MSCs and CMS from hiPSCs. Clinical-grade cells derived from patient-specific hiPSCs could be derived based on our methodology with modification.

We have established a low-cost and efficient methodology for the generation of high quality MSCs from human induced pluripotent stem cells. This methodology also enables the co-generation of cardiomyocytes, which serves as index for good quality of hiPSCs and hESCs. It facilitates the pre-transplantation screening for better lines of MSCs. Such combination of cardiomyocytes and mesenchymal stem cells in cell therapy is likely to increase the cardiac repair efficiency whereby the paracrine factors from iPS-MSCs are able to sustain the survival of both resident myocytes and transplanted myocytes by neoangiogenesis initiated by the co-transplanted iPS-MSCs. Furthermore, the derived MSCs can be used to construct tissue engineered tissues where vascularization is sustained by MSC in forming close partnership with endothelial cells. In addition, the iPS-derived MSCs obviate the problems of cellular senescence and loss of repair capacity experienced in bone marrow derived MSC from the same patients.

Example 2

We hypothesize that CMs and MSCs, both of mesoderm origin, can be generated concurrently from hiPSCs via embryonic body (EB) formation with a pro-mesoderm formation condition. As cardiac differentiation indicates a mesodermal diversion from pluripotency of hiPSCs, MSCs co-obtained could be less of tumorigenic concern, which makes this MSC generation procedure low-cost and more efficient.

In this study, we repeatedly co-generated high quality of CMs and MSCs from single EB-derived from hiPSCs. Both cell types showed functional characteristics that are promising for autologous application in cardiac cell therapy.

Materials and Methods

1. Generation and Characterization of Human Pluripotent Stem Cell Lines

Human iPSC lines, hiPSC (1) and hiPSC (2) were generated in our laboratory from human neonatal dermal fibroblasts (ATCC and LONZA) via retroviral-based reprogramming with Yamanaka factors (Oct-4, Sox-2, c-Myc and Klf-4). In addition, a human embryonic stem cell (hESC) line (H9) was acquired from WiCell Institute, Wisconsin, USA.

Immunocytochemistry hiPSCs grown on feeder cells were subjected to immunocytochemistry assay with mAbs against Oct-4, SSEA-4, TRA 1-60, and TRA 1-81 antibodies (Millipore). Laser confocal microscopic images were taken.

RT-PCR

First-strand cDNA was synthesized from RNA isolated from hiPSC (1) and (2), the dermal fibroblasts and H9 hESCs. Endogenous Oct-4, Sox-2, c-Myc and Klf-4 gene were amplified by semi-quantitative PCR. Primers sequences were adopted from a previous report (Takahashi et al., 2006).

Teratoma formation—$2 \times 10^6$ of hiPSC (1) and (2) were injected into the kidney capsule and hind limb muscle of NOD-SCID mice. Next, tumors were explanted, fixed, paraffin embedded. Sections-were stained with haematoxylin and eosin.

Karyotyping—Chromosomal studies were carried out in the Cytogenetic Lab of KK Women and Children Hospital, Singapore. Standard G-banding chromosome analysis was performed with hiPSC (1) and hiPSC (2) using standard protocols for high resolution G-banding.

2. Generation of hiPSC-CMs and hiPSC-MSCs

Prior to differentiation, hiPSCs and hESCs were maintained on mitomycin C-treated mouse embryonic fibroblasts (MEF) feeder in hESC medium (Final concentrations: 80% Knockout DMEM, 20% Serum replacement, 1% non-essential amino acid, 1 mM L-glutamine, 0.1 mM beta-mercaptoethanol and 4 ng/ml basic Fibroblasts Growth Factor (bFGF), all from Invitrogen).

The CARM/SB differentiation procedure: On Day 1, EBs were formed mechanically from hESC/hiPSC colonies and transfer into 6-well non-adherent dishes and culture in hESC medium w/o bFGF for 24 hours. On Day 2, the CM/MSC differentiation were initiated with a serum-free and insulin-free medium, named CARM (DMEM High Glucose 485 ml, L-Glutamine 5 ml, NEAA 5 ml, Selenium Transferrin 5 ml (Sigma) and 2-mercaptoethanol 3.5 ul) supplemented with SB 203580 (5 uM), a specific p38-MAPK inhibitor (Sigma)

and kept for 4 days till Day 6 when the differentiation medium was changed and maintained till Day 14. Contracting EB aggregates emerged from Day 12. On Day 15, the contracting EB aggregates were picked up and plated on 0.1% gelatin-coated wells of 6-well plate or 3.5 CM Petri dishes in DMEM medium containing 2% FBS and keep for 1 weeks until the contracting CM clumps firmly attached and CM outgrowth enlarged and could be dissected out. In addition, H9, hiPSC (1) and (2) were also differentiated with the EB-20 method in which the EB aggregated were plated on Day 8 before contracting (EB-20 method adapted from He et al., 2003).

3. Isolation and Expansion of hPSC-MSCs

As shown in FIG. 2, following the method, rapid outgrowth of MSC-like cells from the attached EB aggregates were observed immediately after the plating. Those MSC-like cells migrated out and covered >80% of a well of a 6-well plate or a 3.5 CM dish in ~two weeks time. After mechanical removing of the CM clumps and the non-MSC-like cells, the remaining MSC-like cells were cultured in MSC medium (DMED supplemented with 10% serum) to full confluency and dissociated with Trypsin and transferred into a T25 flask (Passage 1). Cells were further expanded in MSC medium with a 1:4 split ratio. MSCs were continually expanded to passage 20 and above.

4. Characterization of hiPSC-CMs

Clumps of contracting CMs were dissected out under a microscope and were enzymatically dissociated. Enzymatically dissociated CMs were seeded on uncoated 3.5 cm Petri dishes and were transferred to a recording chamber mounted on the stage of an inverted microscope (TE2000-S, Nikon, Tokyo, Japan). Whole-cell APs and ion currents were recorded with a Patch-Clamp amplifier (Axon 200B, Axon Instruments). Data acquisition and analysis were performed using Clampex and Clampfit software (version 10.0, Axon Instruments). In the current-clamp mode, the APs were recorded in normal Tyrode's solution. V-CM, A-CM and N-CM were identified by their characteristic APs.

5. Characterization of hiPSC-MSCs

Our hiPSC (1) and hiPSC (2) derived-MSCs, hereby named iMSC (1) and iMSC (2), respectively, were thoroughly characterized. Two lines of human bone marrow-derived MSCs were used in this study as control. BM-MSC (1) was derived from marrow mononuclear cells (DV Biologics, Costa Mesa, Calif.) while BM-MSC (2) was derived from a myocardial infarction patient recruited at National Heart Centre Singapore with a protocol approved by the Institutional Review Board of Singapore Health Science Authority.

Surface Markers Measurement and Cell Sorting

With various passages of iMSC (1), iMSC (2) and hESC-MSCs, Flow Cytometry and Fluorescent-Activated Cell Sorting (FACS) were performed with a BD Aria. PE, APC and FITC congregated mAbs were used to determine CD29, CD44, CD73, CD90, CD105, and CD146 expression. Moreover, pluripotent stem cell markers SSEA-4, TRA-1-60, TRA-1-81 and MHC Class I and II markers (HLA-AC and HLA-DL) were measured. In addition, $CD44^+/CD146^+$ hiPSC-MSCs were sorted out by FACS.

Adipogenic and Osteogenic Differentiation of hiPSC-MSCs

Passage 6 iMSC (1) were differentiated into adipocytes and osteocytes in the corresponding differentiation media from Stemcell Technologies®. The adipocytes and osteocytes were confirmed by Oil-Red-O staining and Alizarin Red S Staining, respectively.

the Growth Kinetics of MSCs iMSC (1) and iMSC (2) were serially cultured to Passage 18. After Passage 2 iMSCs were expanded with a starting density of $1 \times 10^6$ cells per T75 flasks in MSC medium. Cells were split when they reached 90~100% confluence. Next, $1 \times 10^6$ cells were re-seeded again in a T75 culture flask. In the mean time, the growth kinetics of MSCs derived from two bone marrow samples was also determined. The cumulated population doublings level (NPDL) was calculated and plotted.

Telomerase Activity Assay

The telomerase activity of cultured cells was explored using TRAPEZE® telomerase detection kit (Millipore). The procedures in the manual were strictly followed. In brief, the cell extracts (from a total of $5 \times 10^6$) were prepared from cultured iPSC-MSC cells using 3-[(3-cholamidopropyl)-dimethylammonio]-1-propanesulfonate (CHAPS) lysis buffer, and human dermal fibroblasts, HeLa cell and H9 ES cell extracts were prepared as well. Detection of telomerase in cells employed the PCR-based telomeric-repeat amplification protocol (TRAP) described by Kim et al (1994), using the oligonucleotides TS and CX as forward and reverse primers respectively. PCR was performed for 27 cycles with a 30-second denaturation step at 94 degree, 30-second annealing step at 50 degree, and a 1-minute extension step at 72 degree. PCR products were resolved by electrophoresis in nondenaturing 15% polyacrylamide gels in 45 mM Tris base/45 mM boric acid/1 mM EDTA for 1800 V·hr. Gels were stained with 1% SYBR gold for 20 minutes and exposed to UV illumination for documentation.

Teratoma Formation Assay

As above-mentioned, $2 \times 10^6$ of passage 4, iMSCs were injected into the hind limb muscle (im) and kidney capsule of NOD-SCID mice and allowed 12~16 weeks to form teratoma.

Karyotyping

The cytogenetic stabilities of hiPSCs were monitored by Karyotyping. The test was conducted by the Cytogenetic Lab of KK Women and Children Hospital Singapore and Singapore General Hospital following standard protocols. Standard G-banding chromosome analysis including karyotype of trisomy 21 was performed with selected hiPSC lines using standard protocols for high resolution G-banding.

Matrigel-Based Tube Formation Assay

Matrigel (BD) of 75 µL was added in each wells of a 96-well plate. Unsorted and $CD44^+/CD146^+$ iPSC-MSCs (P6-P11) and unsorted BM-MSCs (P3), with a total number of $0.6 \times 10^4$, were seeded on Matrigel together with $1.25 \times 10^4$ human umbilical vein endothelial cells or HUVECs (Invitrogen) at P3. After 24 hours, vessel-like network structures were examined under light microscopy and images were taken. Next, cells were fixed and the vasculature were stained by anti-human-CD31 monoclonal antibody for HUVECs and anti-human alpha-Smooth Muscle Actin (α-SMA) for MSCs and viewed under a fluorescent microscope. Vasculature density was calculated as the lengths and thickness of vessels/$mm^2$ using Image J software.

Wound-Healing Assay

Human neonatal dermal fibroblasts (P8) were cultured to 90% confluence and a 2-mm wide gap was created by scratching. Next, the conditioned-medium of iMSC(P6) and BM-MSC(P4) were collected after 24 hours culturing in serum-free DMEM and added to the fibroblasts culture and incubated for 24 hours. Light microscopy images were taken and the remaining gap area was measured and quantified by Image J software.

6. In Vivo Functional Assays

Myocardial infarction model was generated in severe combined immunodeficiency (SCID) mice by ligation of the left anterior descending artery or LAD. Next, a total of $2 \times 10^5$ iPSC-derived MSCs, or $2 \times 10^5$ iPSC-derived cardiomyocytes-like cells, or $1 \times 10^5$ iPS-derived MSCs in combination of $1 \times 10^5$ iPSC-derived cardiomyocytes-like cells were injected into the peri-infarct site. iPSC-derived MSCs were labeled with green fluorescent protein (GFP) so they could be better tracked in the post-infarct heart. Cardiac hemodynamic were performed at 8 weeks post transplantation by echocardiography.

7. Statistical Analysis

The data was—expressed as mean %±SD. Where appropriate, data was—analyzed by 2-tailed Student t tests. A p values below 0.05 were considered to be statistically significant.

Results

1. Generation and Characterization of hiPSCs

Figure 1:
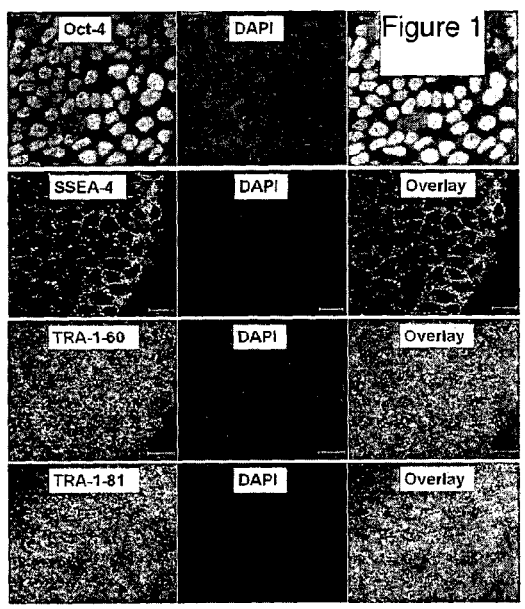
FIG. 1 Characterization of hiPSCs
Figure 1:
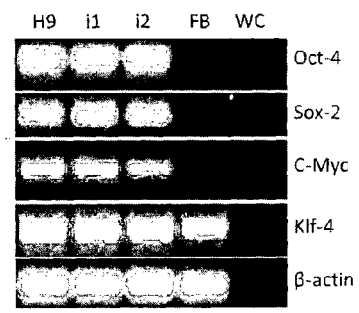
Figure 1:
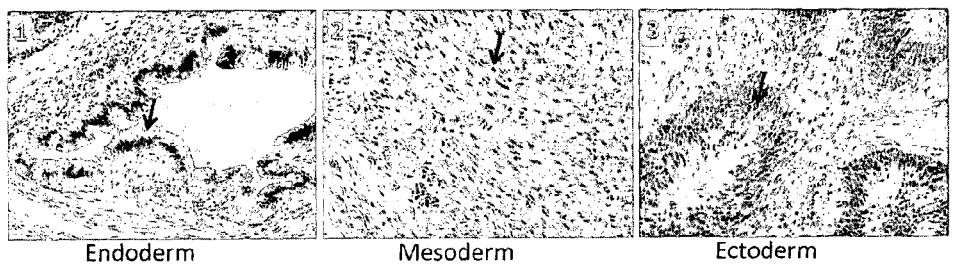
Figure 1:
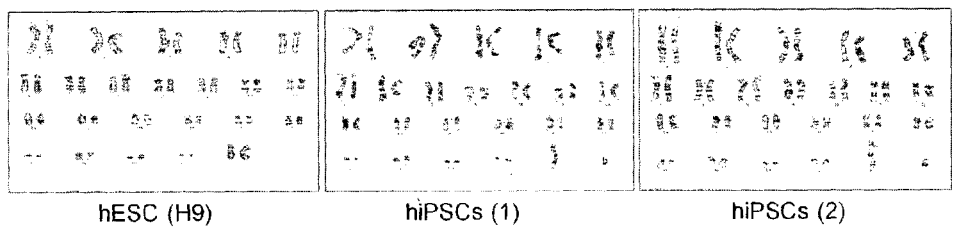

Concordance with our previous report of virus-free iPSC, the current viral approach of reprogramming dermal fibroblasts gave rise to iPSC colonies with typical ESC-like colonies in approximately 18 days post retroviral transduction. Their doubling rates were comparable to the similarly maintained H9 hESC cell line. Eight individual clones were selected for further studies based on alkaline phosphatase staining. Further immunocytochemistry staining confirmed that all hiPSC clones expressed pluripotent stem cell markers, Oct-4, SSEA-4, TRA1-60 and TRA-1-81. Moreover, their endogenous expression of Oct-4, Sox-2, KIf-4 and c-Myc were validated by RT-PCR. Among them, 2 iPSC clones, hiPSC (1) and hiPSC (2), that maintained excellent undifferentiated culture in successive passages were selected for further in-depth studies. Both clones showed normal karyotypes that were similar to the well characterized H9 hESC line. Moreover, its pluripotency was confirmed by teratoma formation in vivo with phenotypes of 3-germ layers consisting of cartilage (mesoderm), neuroepithelial rosette (ectoderm) and gut epithelium (endoderm) following renal capsule implant in SCID mice at week 12. FIG. 1 shows the characterization result of hiPSC (1).

2. Co-Generation of CMs and MSCs from hiPSCs

Embryoid bodies created from undifferentiated colonies of hiPSC were differentiated towards cardiomyocytes in the present CARM/SB protocol or EB-20 protocol. FIG. 2 presents a graphical demonstration for generating CMs and MSCs from hiPSC (1) and (2) and H9 hESCs. Higher cardiac differentiation efficiency (20~30% for hiPSCs and ~50% for hESCs) was achieved with CARM/SB protocol (FIG. 3). In addition, no appreciable difference in the quality of CMs including maturity and proportion of ventricular-like (V), atrial-like (A), and nodal-like (N) cardiomyocytes between the two differentiation protocols was noted (FIG. 3). Over 30% of contracting EB aggregates plated gave rise to contracting aggregates of CMs and associated fibroblastic outgrowth of MSC-like cells. However, in contrast to EB20 protocol that yielded a heterogeneous outgrowth of different cell types, the present CARM/SB protocol resulted in a homogeneous outgrowth of MSC-like cell population that rapidly migrated from the attached CM clusters. Compared to the CARM/SB derived MSCs, no persistent MSC lines could be generated from the EB20 protocol since MSC-like cells failed to achieve cellular homogeneity even after repeated passages in culture.

3. Characterization of iMSCs

3.1 iMSCs Expressed Typical MSC Surface Markers

In contrast to parental hiPSC lines, the expanded iMSC (1) and iMSC (2) expressed no SSEA-3, SSEA-4, TRA-1-60 and TRA-1-80. iMSC (1), (2) and hESC-MSCs expressed CD29, CD44, CD73, CD90, and CD105 that typified adult MSCs (FIG. 4B). Low MHC-I marker HLA-ABC and no MHC-II marker (HLA-DL) were detected. FIG. 4 shows representative results from iMSC (1). While no pluripotent stem cell markers were detected with passage 2 iMSC (1) (FIG. 4A), the typical MSC markers were maintained with stable expression at passages 2, 9 and 19 (FIG. 4B). Moreover, CD146, a pro-angiogenic marker of MSCs was found to maintain its expression until late passages (FIG. 4B), even though its expression was known to diminish in adult MSCs after successive passages in culture. Furthermore, low MHC-I marker (HLA-ABC) and no MHC-II marker (HLA-DL) were detected (FIG. 4C).

3.2 iMSCs were Capable of Lineage-Specific Differentiations

Consistent with MSC characteristics, iMSC (1) and iMSC (2) at passages 7 were found to show adipogenic and osteogenic differentiation with fatty droplets and mineralized calcium deposits that were confirmed by Oil red-O and Alizarin red-S staining respectively (FIG. 5).

3.3 iMSCs were Safe from Tumorigenesis and Cytogenetic Abnormalities

In the same teratoma formation experiment which involves hiPSC (1) and (2), passage 2 iMSCs failed to form teratoma when transplanted into renal capsule of SCID mice. In addition, normal karyotype of iMSCs at younger and older passages was confirmed (FIG. 6C).

3.4 iMSCs Showed a Robust Growth Potential

Similar to hESC-MSCs, the two iMSC lines showed robust growth kinetic as demonstrated by over 30 cumulative population doublings in continuous culture without signs of cellular senescence. In comparison, the two BM-MSC lines could not be expanded to more than passage 9 with a drastic slowing of growth rates and loss of fibroblastic cellular morphology (FIG. 6). Consistently, the robust proliferation rates of iMSCs coincided with a relatively sustained telomerase activity which was similar to HeLa tumor cell line or the pluripotent H9 hESC line. In contrast, the parental line of human dermal fibroblasts (HDF, passage 3) showed a diminished telomerase activity (FIG. 6).

3.5 iMSCs Showed a Marked Pro-Angiogenic Potential

Consistent with previous reported enhanced pro-angiogenic activity of hiPSC-derived MSCs in comparison to BM-MSCs, our hiPSC-MSCs demonstrated superior angiogenic activity. When co-cultured with HUVEC, CD146$^+$ sorted hiPSC-MSC promoted more extensive vascular network and more mature tubule formation in length and caliber of vascular structures as compared to. HUVEC alone or co-cultured with unsorted hiPSC-MSCs. In contrast, BM-MSCs failed to show either effect. Moreover, there was marked co-localization of hiPSC-MSCs as peri-vascular cells in the HUVECs constituted vascular network (FIG. 7).

3.6 iMSCs Showed a Marked Tissue Healing Potential

Conditioned medium derived from MSCs is known to contain important growth factors such as FGF and (vascular endothelial growth factor (VEGF) that are important for therapeutic effect of MSCs. Consistent with augmented reparative property, conditioned medium harvested from our hiPSC-MSCs induced a more robust migration of fibroblasts in an vitro wound healing model as compared to conditioned media from either BM-MSC or DMEM alone. There was earlier migratory response and superior in growth of fibroblasts into the created tracks. Moreover, such effect of hiPSC-MSC was sustained even in late passage in culture. The effect of iMSC (1) conditioned medium on fibroblast wound healing was shown in FIG. 8.

3.7 iMSCs and CMs were Free of Teratoma Formation

No tumor like structures were found in the heart and other part of the mice transplanted with iPSC-derived cells.

3.8 iMSCs Showed Potential Clinical Benefits

Myocardial infarction (MI) in SCID mice generated by ligating the left anterior descending artery showed depressed cardiac function. Compared to post-infarcted cardiac function, acute injection of GFP labeled iPS-derived MSCs showed a better preserved ejection fraction (−0.9±9.6% vs. −9.6±1.6%) and fractional shortening (−1.2±7.2% vs. −7.4±0.5%) relative to untreated infracted animals at 8 weeks post cell transplantation.

Discussion

Large quantities of CMs and supporting parenchymal cells such as endothelial cells and smooth muscle cells are needed for meaningful cardiac cell therapy in post myocardial infarction. Paracrine effect derived from MSCs play an important role in cardiac repair by promoting endothelial angiogenesis. Similar to pluripotent hESCs, patient-derived iPSCs can be cryopreserved and repeatedly used to generate specific cell lineages such as CMs and MSCs. Given the supportive role of MSCs in cell therapy, a collective administration of both CMs and MSCs may be important for cardiogenesis and angiogenesis for cardiac repair.

Currently hiPSC-CMs and iPSC-MSCs are separately derived through a laborious process. While cardiac differentiation was achieved via EBs formation, hESCs and hiPSCs were 2D differentiated to MSCs, mechanically isolated, FACS sorted and clonally derived through single cell dilution to yield homogeneous population of MSCs. In this study, CMs and MSCs were simultaneously derived from a single EB using the present CARM/SB protocol, a serum-free insulin-free cardiac differentiation medium supplemented with a specific inhibitor for the p38-MAKP, SB203580 and compared to another well-adopted serum containing differentiation protocol, EB-20. Compared to EB-20 protocol, marginally higher cardiac differentiation efficiency was achieved with the present method while the quality of CMs including sarcomeric structures and proportion of ventricular, atrial, and nodal cardiomyocytes were similar between these two methods (FIG. 2). On the other hand, the generation of a large number and high quality of iMSCs could bring more remarkably value to regenerative medicine.

Our iMSCs meet the criteria for human MSCs set by the Mesenchymal and Tissue Stem Cell Committee of the International Society for Cellular Therapy. Our iMSCs were multipotent and expressed typical MSC markers (CD29, CD44, CD73, CD90, and CD105), but not hematopoietic markers CD45 and CD34 associated with bone marrow-derived cells.

The present CARM/SB protocol consistently yielded homogeneous MSCs from the outgrowth of beating EB aggregates plated. However, the EB-20 method which uses 20% serum with early (8 days) plating of EB aggregates, failed to generate homogeneous MSCs. Successful generation of homogeneous MSCs by the present CARM/SB protocol could be due to several factors: 1) the SB203580 and insulin-free differentiation medium, 2) serum-free differentiation medium may prevent excessive outgrow of mixed cell lineages from three germ layers, and 3) prolonged suspension culturing of EBs aggregates (till 15 days) may withhold excessive growth of various cell lineages. Large quantities of transplantable cells are critical for cell therapy since cell loss during and after cell transplantation is substantial. However, due to the limited self-renewal potential and lower functional potency associated with aging and chronic diseases, in vivo studies suggested that human MSCs with a passage number below 6 are ideal for retaining sufficient reparative capacity. Furthermore, clinical trials indicated that a total of $10^7$~$10^8$ or $5\times10^6$/kg MSCs will be required for clinical application. In addition, repeated generation of large numbers of young and functional-specific subpopulation of MSCs may be needed to sustain therapeutic efficacy in repeat injections. However, it is only feasible to obtain, from a single aspiration of bone marrow, sufficient MSCs which could for a single delivery rather than repeated injections, there is no possibility of further isolation of functional subpopulations. In contrast, our hiPSC lines showed robust self-renewal potential that is consistent with previously reported hESC-MSCs and hiPSC-MSCs. With our protocol, several folds of iMSCs (compared to BM-MSCs) could be generated from a hiPSC line.

The safety of iMSCs remains a major concern for clinical application. This particularly concerns iMSCs since they are derived from pluripotent iPSCs with prolonged cultural period. In this study, our iMSCs showed no expression of SSEA-3, SSEA-4, TRA-1-60 and TRA-1-81 and no teratoma formation despite obviating FACS sorting or clonal derivation from single cell colonies. Our data suggests that no pluripotent stem cell contamination. Furthermore, karyotypes of our hiPSC-MSCs remained normal after successive expansion in culture.

Pro-angiogenic effect of MSCs has been documented in post-MI cardiac repair and ischemic limbs. MSCs have been suggested to function as pericytes or perivascular cells in supporting endothelial cell to form vascular networks in which MSCs are indispensable for the formation of functional competent vasculature without leakage. Consistently, our results showed that hiPSC-MSCs acted cooperatively with HUVECs to form extensive tube-like vascular structures further supporting their perivascular role in angiogenesis.

Furthermore, our hiPSC-MSCs retained stronger pro-angiogenic effect at passage 12 than BM-MSCs at passage 3. In addition, the $CD44^+/146^+$ sorted hiPSC-MSCs showed a better pro-angiogenic effect than unsorted hiPSC-MSCs. Consistent with pro-wound healing effect of MSCs, hiPSC-MSCs demonstrated a superb healing effect in promoting cellular migration and tissue coalescence than that of BM-MSCs. Collectively, our iPSC-MSCs exhibit substantial paracrine protective effects that may well support substantial tissue repair when transplanted together with concurrently generated CMs for autologous cell therapy.

The safety and potential clinical benefits of iMSCs and CMs proved with the animal study suggest that hiPSC-derived CMs and MSCs could be of great clinical potential.

Overview

Cardiomyocytes (CMs) and mesenchymal stem cells (MSCs) are important cell types for cardiac repair post myocardial infarction. We hypothesized that both CMs and MSCs can be generated simultaneously from human induced pluripotent stem cells (hiPSCs) via a pro-mesoderm differentiation strategy.

Materials and Methods:

Two hiPSC lines, hiPSC (1) and (2) were generated from human neonatal dermal fibroblasts via retroviral-based reprogramming. H9 human embryonic stem cells (hESCs) served as control. In addition, bone marrow (BM)-MSCs from a healthy control (BM-MSC (1)) and a myocardial infarction patient (BM-MSC(2)) were used as control for MSC characterization.

Results:

From hiPSCs and hESCs, embryoid bodies (EBs) were differentiated in a serum-free and insulin-depleted medium containing a p38 MAPK inhibitor, SB 203580 to co-generate CMs and MSCs repeatedly. Comparatively, a serum containing differentiation protocol showed similar cardiac differentiation efficiency, but failed to generate homogeneous MSCs. hiPSC-derived CMs showed proper cardiac action potential by whole cell patch-clamp. Moreover, hiPSC-derived MSCs (iMSCs) generated by the present CARM/SB method expressed common MSC markers and were capable of adipogenesis and osteogenesis. Compared to bone marrow (BM)-MSCs, iMSCs were expanded more than 32 population doublings without showing cell senescence and showed superior pro-angiogenic and wound healing properties.

Discussion:

We generated a large numbers of homogeneous MSCs in a low-cost, and efficient manner simultaneously with derivation of CMs. Functionally competent CMs and MSCs co-generated from hiPSCs may be used for autologous cardiac repair.

Key Words:

induced pluripotent stem cells, cardiomyocytes, mesenchymal stem cells, angiogenesis.

Acknowledgement:

This study is funded by National Research Foundation of Singapore (NRF2008 NRF-CRP001-068).

REFERENCES

He et al., (2003) Circulation research 93:32-39.
Kim et al., (1994) Specific association of human telomerase activity with immortal cells and cancer. Science 266: 2011-2015.
Lien et al., (2007) Derivation of clinically compliant MSCs from CD105+, CD24− differentiated human ESCs. Stem Cells 25(2):425-436.
Takahashi et al., (2006) Induction of pluripotent stem cells from mouse embryonic and adult fibroblast cultures by defined factors. Cell 126:663-676.

The invention claimed is:

1. A method for preparing induced pluripotent stem cell-derived mesenchymal stem cells and induced pluripotent stem cell-derived cardiomyocyte cells comprising the steps of:
   (i) providing one or more induced pluripotent stem cells;
   (ii) forming one or more embryoid bodies from the induced pluripotent stem cells using a non-adherent substrate;
   (iii) contacting the embryoid bodies with serum-free and insulin-free medium comprising a p38-MAPK inhibitor to form aggregates of contracting embryoid body cells;
   (iv) transferring at least one contracting embryoid body aggregate to a cell-culture treated substrate and contacting the contracting embryoid body aggregates with a medium comprising ≤5% serum to form a population of cells comprising induced pluripotent stem cell-derived mesenchymal stem cells and aggregates of induced pluripotent stem cell-derived cardiomyocyte cells, wherein the population of cells is substantially adhered to the substrate.

2. The method according to claim 1, comprising detaching the adhered cells from the substrate and collecting the detached cells as a population of induced pluripotent stem cell-derived mesenchymal stem cells and induced pluripotent stem cell-derived cardiomyocyte cells.

3. The method according to claim 1, comprising separating the aggregates of induced pluripotent stem cell-derived cardiomyocyte cells from the induced pluripotent stem cell-derived mesenchymal stem cells to give an isolated population of induced pluripotent stem cell-derived cardiomyocyte cells and an isolated population of induced pluripotent stem cell-derived mesenchymal stem cells.

4. The method according to claim 3, wherein the isolated population of induced pluripotent stem cell-derived mesenchymal stem cells is homogeneous.

5. The method according to claim 3, comprising culturing the isolated population of induced pluripotent stem cell-derived mesenchymal stem cells.

6. The method according to claim 3, further comprising maintaining the isolated population of induced pluripotent stem cell-derived mesenchymal stem cells in culture.

7. The method according to claim 3, wherein the isolated population of induced pluripotent stem cell-derived cardiomyocyte cells comprises ventricular-like, atrial-like and nodal-like cardiomyocytes.

8. The method according to claim 3, further comprising culturing the isolated population of induced pluripotent stem cell-derived cardiomyocyte cells.

9. The method according to claim 3, further comprising maintaining the isolated population of induced pluripotent stem cell-derived cardiomyocyte cells in culture.

10. The method according to claim 1, wherein step (ii) comprises contacting the induced pluripotent stem cells with a suitable culture medium to form one or more embryoid bodies.

11. The method according to claim 1, wherein step (iii) comprises contacting the embryoid bodies with a serum-free and insulin-free medium comprising a p38-MAPK inhibitor for at least 8 days.

12. The method according to claim 1, wherein the serum-free and insulin-free medium of step (iii) comprises the p38-MAPK inhibitor 4-[4-(4-fluorophenyl)-2-(4-methylsulfinylphenyl)-1H-imidazol-5-yl]pyridine, 1-[5-tert-butyl-2-(4-methylphenyl)pyrazol-3-yl]-3-[4-(2-morpholin-4-ylethoxy)naphthalen-1-yl]urea, 4-[4-(4-fluorophenyl)-5-pyridin-4-yl-1,3-dihydroimidazol-2-ylidene]cyclohexa-2,5-dien-1-one, 6-(N-carbamoyl-2,6-difluoroanilino)-2-(2,4-difluorophenyl)pyridine-3-carboxamide, 5-[2-tert-butyl-4-(4-fluorophenyl)-1H-imidazol-5-yl]-3-(2,2-dimethylpropyl)imidazo[4,5-b]pyridin-2-amine; methanesulfonic acid, 5-(2,6-dichlorophenyl)-2-(2,4-difluorophenylthio)-6H-pyrimido[1,6-b]pyridazin-6-one or 3-[3-bromo-4-[(2,4-difluorophenyl)methoxy]-6-methyl-2-oxopyridin-1-yl]-N,4-dimethylbenzamide.

13. The method according to claim 1, wherein the medium of step (iv) comprises 0.5 to 5% serum.

14. The method according to claim 1, wherein the serum of step (iv) comprises fetal bovine serum (FBS).

15. The method according to claim 1, wherein the induced pluripotent stem cells comprises human induced pluripotent stem cells.

* * * * *